(12) United States Patent
Lehmann et al.

(10) Patent No.: US 6,172,824 B1
(45) Date of Patent: Jan. 9, 2001

(54) LOW LOSS PRISM RETROREFLECTORS FOR RELATIVE INDEX OF REFRACTION LESS THAN THE SQUARE ROOT OF 2

(75) Inventors: Kevin K. Lehmann, Lawrenceville; Paul Rabinowitz, Bridgewater, both of NJ (US)

(73) Assignee: Trustees of Princeton University, Princeton, NJ (US)

( * ) Notice: Under 35 U.S.C. 154(b), the term of this patent shall be extended for 0 days.

(21) Appl. No.: 09/494,161

(22) Filed: Jan. 24, 2000

Related U.S. Application Data

(63) Continuation-in-part of application No. 09/412,069, filed on Oct. 4, 1999, now Pat. No. 6,097,555, which is a continuation of application No. 08/955,126, filed on Oct. 21, 1997, now Pat. No. 5,973,864.

(51) Int. Cl.[7] .............................. G02B 5/04; G01J 3/00; G01N 21/00; H01S 3/08

(52) U.S. Cl. .................. 359/834; 359/836; 359/837; 372/92; 372/93; 372/94; 372/100; 356/300; 356/436; 356/445

(58) Field of Search ..................... 359/831, 833, 359/834, 835, 836, 837, 669; 356/300, 436, 437, 438, 439, 445; 372/16, 72, 92, 93, 94, 95, 100

(56) References Cited

U.S. PATENT DOCUMENTS

| | | |
|---|---|---|
| 1,719,443 | * 7/1929 | Nichterlein . |
| 3,402,364 | 9/1968 | De Lang . |
| 3,711,788 | 1/1973 | Forkner . |
| 3,976,368 | * 8/1976 | McCann et al. . |
| 3,982,203 | 9/1976 | De Wit . |
| 4,161,436 | 7/1979 | Gould . |
| 4,525,034 | 6/1985 | Simmons . |
| 4,578,793 | * 3/1986 | Kane et al. . |
| 4,677,639 | 6/1987 | Sasser . |
| 4,740,986 | 4/1988 | Reeder . |
| 4,746,201 | 5/1988 | Gould . |
| 5,276,548 | 1/1994 | Margalith . |
| 5,463,493 | 10/1995 | Shah . |

(List continued on next page.)

FOREIGN PATENT DOCUMENTS 63-013386  1/1988 (JP) .

OTHER PUBLICATIONS

International Search Report dated Jan. 29, 1999.
J. White, Long Optical Paths of Large Aperture, 32 *J. Opt. Soc. Amer.*, 285 (May, 1942).
D. Heriott et al., Off–Axis Paths in Spherical Mirror Interferometers, 3 *Appl. Opt.* (4), 523 (Apr., 1964).

(List continued on next page.)

*Primary Examiner*—Ricky D. Shafer
(74) *Attorney, Agent, or Firm*—Ratner & Prestia

(57) ABSTRACT

A stable resonator for a ring-down cavity spectroscopy cell having an optic axis. The resonator includes two Brewster's angle retroreflector prisms, at least one prism having greater than two total internal reflection surfaces. The prisms are disposed in alignment along the optic axis of the resonator. One or both of the prisms can be rotated so that light rays enter and leave a surface of the prism nearly at Brewster's angle to the normal of the prism surface. This feature maintains alignment between the prisms and allows the resonator to be tuned. One of the total internal reflection surfaces of at least one of the prisms may be a curved surface (either a ground curved surface or a surface curved by the addition, through optically contacting or gluing, of a plano-convex lens to the surface). In a preferred embodiment, at least one of the prisms has an apex angle of about 180° minus two times Brewster's angle, a second angle of about 90° plus the angle of incidence minus Brewster's angle, and a third angle of about three times Brewster's angle plus the angle of incidence for internal reflection minus 90°.

34 Claims, 15 Drawing Sheets

U.S. PATENT DOCUMENTS

| | | |
|---|---|---|
| 5,483,342 | 1/1996 | Rockwell . |
| 5,528,040 | 6/1996 | Lehmann . |
| 5,835,231 | 11/1998 | Pipino . |
| 5,912,740 | 6/1999 | Zarc et al. . |
| 5,973,864 * | 10/1999 | Lehmann et al. .................... 359/834 |
| 6,097,555 * | 8/2000 | Lehmann et al. .................... 359/834 |

OTHER PUBLICATIONS

A. O'Keefe & D. Deacon, Cavity Ring–Down Optical Spectrometer for Absorption Measurements Using Pulsed Laser Sources, 59 *Rev. Sci. Instrum.*, 2544 (Dec., 1988).

D. Romanini & K. Lehmann, Ring–Down Cavity Absorptionn Spectroscopy of the Very Weak HCN Overtone Bands with Six, Seven, and Eight Stretching Quanta, 99 *J. Chem. Phys.* (9), 6287 (Nov. 1.

G. Rempe et al., Measurement of Ultralow Losses in an Optical Interferometer, 17 *Opt. Letters* (5), 363 (Mar. 1, 1992).

T. Yu & M. Lin, Kinetics of Phenyl Radical Reactions Studied by the "Cavity–Ring–Down" Method, 115 *J. Am. Chem. Soc.*, 4371 (1993).

G. Meijer et al., Coherent Cavity Ring Down Spectroscopy, 217 *Chemical Physics Letters* (1,2), 112 (Jan. 7, 1994).

J. Scherer et al., Cavity Ring Down Dye Laser Spectrosopy of Jet–Cooled Metal Clusters: $CU_2$ and $CU_3$, 172 *Chemical Physics Letters* (3,4), 214 (Sep. 7, 1990).

F. Stoelkel & G. Atkinson, Time Evolution of a Broadband Quasi–cw Dye Laser: Limitation of Sensitivity in Intracavity Laser Spectroscopy, 24 *Applied Optics* (21), 3591 (Nov. 1, 1985).

K. Lehmann & D. Romanini, Molecules in the Stellar Environment, *Experimental Measurement of Weak Band Intensities in Molecules in the Stellar Environment*, (Springer, 1994).

G. Gould et al., Crossed Roof Prism Interferometer, 1 *Applied Optics* (4), 533 (Jul. 1962).

A. Pipino et al., Evanascent Wave Cavity Ring–Down Spectroscopy with a Total–Internal Reflection Minicavity, 68 (8) *Rev. Sci. Instrum.*, 2978 (Aug. 1997).

* cited by examiner

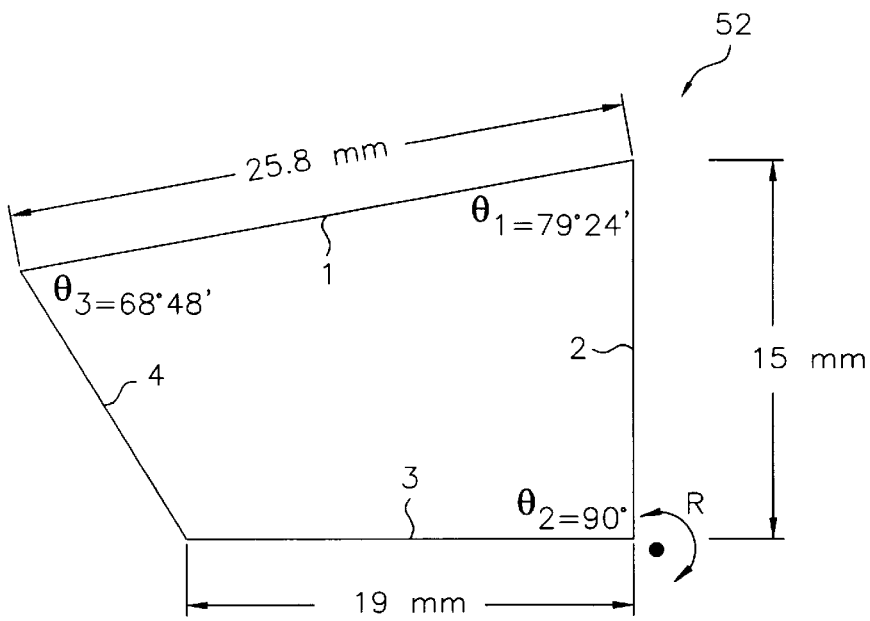
FIG. 9A
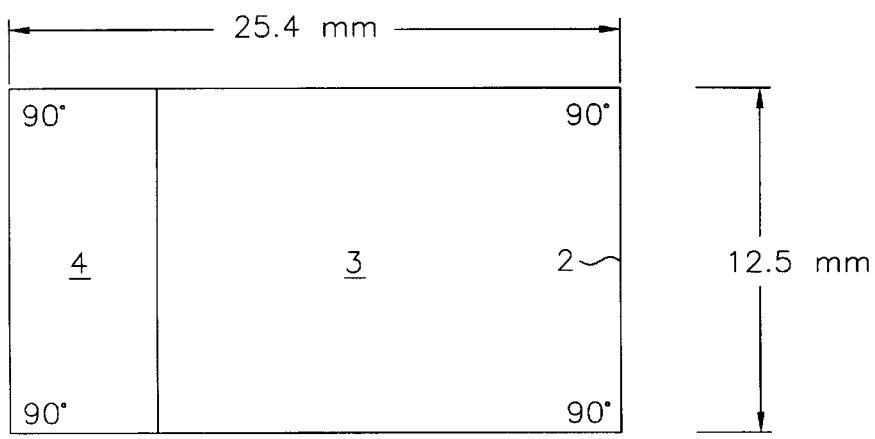
FIG. 9B

LOW LOSS PRISM RETROREFLECTORS FOR RELATIVE INDEX OF REFRACTION LESS THAN THE SQUARE ROOT OF 2

This application is a continuation-in-part of U.S. patent application Ser. No. 09/412,069, filed on Oct. 4, 1999, now U.S. Pat. No. 6,097,555 which is a continuation of U.S. patent application Ser. No. 08/955,126 filed on Oct. 21, 1997, now U.S. Pat. No. 5,973,864.

FIELD OF THE INVENTION

This invention relates generally to absorption spectroscopy and, in particular, is directed to the use of a stable, high-finesse optical resonator for ring-down cavity spectroscopy which incorporates Brewster's angle prism retroreflectors.

BACKGROUND OF THE INVENTION

Referring now to the drawing, wherein like reference numerals refer to like elements throughout, FIG. 1 illustrates the electromagnetic spectrum on a logarithmic scale. The science of spectroscopy studies spectra. In contrast with sciences concerned with other parts of the spectrum, optics particularly involves visible and near-visible light—a very narrow part of the available spectrum which extends in wavelength from about 1 mm to about 1 nm. Near visible light includes colors redder than red (infrared) and colors more violet than violet (ultraviolet). The range extends just far enough to either side of visibility that the light can still be handled by most lenses and mirrors made of the usual materials. The wavelength dependence of optical properties of materials must often be considered.

Absorption-type spectroscopy offers high sensitivity, response times on the order of microseconds, immunity from poisoning, and limited interference from molecular species other than the species under study. Various molecular species, but especially simple molecules such as water, can be detected or identified by absorption spectroscopy. Thus, absorption spectroscopy provides a general method of detecting important trace species. In the gas phase, the sensitivity and selectivity of this method is optimized because the species have their absorption strength concentrated in a set of sharp spectral lines. The narrow lines in the spectrum can be used to discriminate against most interfering species.

In many industrial processes, the concentration of trace species in flowing gas streams must be measured and analyzed with a high degree of speed and accuracy. Such measurement and analysis is required because the concentration of contaminants is often critical to the quality of the end product. Gases such as $N_2$, $O_2$, $H_2$, Ar, and He are used to manufacture integrated circuits, for example, and the presence in those gases of impurities such as water—even at parts per billion (ppb) levels—is damaging and reduces the yield of operational circuits. Therefore, the relatively high sensitivity with which water can be spectroscopically monitored is important to manufacturers of high-purity gases used in the semiconductor industry. Various impurities must be detected in other industrial applications.

Spectroscopy has obtained parts per million (ppm) level detection for water in high-purity gases. Detection sensitivities at the ppb level are attainable in some cases. Accordingly, several spectroscopic methods have been applied to such applications as monitoring water content in gases, including: absorption measurements in traditional long pathlength cells, photoacoustic spectroscopy, frequency modulation spectroscopy, and intracavity laser absorption spectroscopy. These methods have several features, discussed in U.S. Pat. No. 5,528,040 issued to Lehmann, which make them difficult to use and impractical for industrial applications. They have been largely confined, therefore, to laboratory investigations.

In contrast, cavity ring-down spectroscopy (CRDS) has become an important spectroscopic technique with applications to science, industrial process control, and atmospheric trace gas detection. CRDS has been demonstrated as a technique for the measurement of optical absorption that excels in the low-absorbance regime where conventional methods have inadequate sensitivity. CRDS utilizes the mean lifetime of photons in a high-finesse optical resonator as the absorption-sensitive observable.

Typically, the resonator is formed from a pair of nominally equivalent, narrow band, ultra-high reflectivity dielectric mirrors, configured appropriately to form a stable optical resonator. A laser pulse is injected into the resonator through a mirror to experience a mean lifetime which depends upon the photon round-trip transit time, the length of the resonator, the absorption cross section and number density of the species, and a factor accounting for intrinsic resonator losses (which arise largely from the frequency-dependent mirror reflectivities when diffraction losses are negligible). The determination of optical absorption is transformed, therefore, from the conventional power-ratio measurement to a measurement of decay time. The ultimate sensitivity of CRDS is determined by the magnitude of the intrinsic resonator losses, which can be minimized with techniques such as superpolishing that permit the fabrication of ultra-low-loss optics.

At present, CRDS is limited to spectroscopic regions where high reflectivity dielectric mirrors can be used. This has significantly limited the usefulness of the method in much of the ultraviolet and infrared regions, because mirrors with sufficiently high reflectivity are not presently available. Even in regions where suitable dielectric mirrors are available, each set of mirrors only allows for operation over a small range of wavelengths, typically a fractional range of a few percent. Further, construction of many dielectric mirrors requires use of materials that may degrade over time, especially when exposed to chemically corrosive environments. Because these present limitations restrict or prevent the use of CRDS in many potential applications, there is a clearly recognized need to improve upon the current state of the art with respect to resonator construction.

The article by A. Pipino et al., "Evanescent wave cavity ring-down spectroscopy with a total-internal reflection minicavity," Rev. Sci. Instrum. 68 (8) (August 1997), presents one approach to an improved resonator construction. The approach uses a monolithic, total internal reflection (TIR) ring resonator of regular polygonal geometry (e.g., square and octagonal) with at least one convex facet to induce stability. A light pulse is totally reflected by a first prism located outside and in the vicinity of the resonator, creating an evanescent wave which enters the resonator and excites the stable modes of the resonator through photon tunneling. The absorption spectrum of matter located at the totally reflecting surfaces of the resonator is obtained from the mean lifetime of a photon in the monolithic resonator, which is extracted from the time dependence of the signal received at a detector by out coupling with a second prism (also a totally reflecting prism located outside, but in the vicinity of, the resonator). Thus, optical radiation enters and exits the resonator by photon tunneling, which permits precise control of input and output coupling. A miniatureresonator realization of CRDS results and the TIR-ring resonator extends the CRDS concept to condensed matter spectroscopy. The broadband nature of TIR circumvents the narrow bandwidth restriction imposed by dielectric mirrors in conventional gas-phase CRDS. The work of A. Pipino et al. is only applicable to TIR spectroscopy, which is intrinsically limited to short overall absorption pathlengths, and thus powerful absorption strengths. In contrast, the present invention provides long absorption pathlengths and thus allows for detection of weak absorption strengths.

It is also possible to build a resonator out of two Brewster's angle roof prisms with crossed axes, as described in Gould et al., "Crossed Roof Prism Interferometer," Appl. Opt., Vol. 1, 533–34 (1962). The advantage of this resonator is that it remains aligned for any small angle deviation of the prisms. The disadvantage is that the Brewster's angle of one of the prisms must be set by construction, i.e., the Brewster's angle cannot be adjusted for wavelength by rotation of the prism. There are applications (e.g., at specific wavelengths) where the robust alignment of such a resonator is sufficiently desirable that the loss of the ability to tune the Brewster's angle can be tolerated. The inability to adjust Brewster's angle, however, restricts its application. Furthermore, the resonator described by Gould et al. is not optically stable, and thus cannot be used to produce a low-loss resonator, due to diffraction.

To overcome the shortcomings of the known approaches to improved resonator construction, a new high-finesse resonator (or optical resonator) for CRDS is provided. An object of the present invention is to replace the conventional dielectric mirrors with Brewster's angle prism retroreflectors, thereby providing an improved resonator. A related object is to circumvent the narrow bandwidth restriction of conventional dielectric mirrors used in CRDS. Another related object is to expand the variety of potential applications for CRDS.

It is still another object of the present invention to provide a resonator which incorporates materials that do not degrade significantly over time, even in chemically corrosive environments. An additional object is to enable "tuning," or alignment, of the resonator by rotating the prisms of the resonator. Yet another object of the present invention is to provide an innovative CRDS resonator design that achieves a low intrinsic energy loss and a well-defined relationship between photon decay time and absorption.

SUMMARY OF THE INVENTION

To achieve these and other objects, and in view of its purposes, the present invention provides a stable resonator for a ring-down cavity spectroscopy cell having an optic axis. The resonator includes two Brewster's angle retroreflector prisms, at least one prism having greater than two total internal reflection surfaces. The prisms are disposed in alignment along the optic axis of the resonator. One or both of the prisms can be rotated independently so that light rays enter and leave a surface of the prism nearly at Brewster's angle to the normal of the prism surface. This feature maintains alignment between the prisms and allows the resonator to be tuned. One of the total internal reflection surfaces of at least one of the prisms may be a curved surface (either a ground and polished curved surface or a surface curved by the addition, through optically contacting or gluing, of a plano-convex lens to the surface). In a preferred embodiment, at least one of the prisms has an apex angle of about 180° minus two times Brewster's angle, a second angle of about 90° plus the angle of incidence for internal reflection minus Brewster's angle, and a third angle of about three times Brewster's angle plus the angle of incidence for internal reflection minus 90°.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 9A is a top view of the preferred prism used in the resonator shown in FIG. 8;

FIG. 9B is a back view of the prism of FIG. 9A;

DETAILED DESCRIPTION OF THE INVENTION

The entire disclosure of U.S. patent application Ser. No. 08/955,126, filed on Oct. 21, 1997, now U.S. Pat. No.

5,973,864, and pending U.S. patent application Ser. No. 09/412,069, filed on Oct. 4, 1999, are expressly incorporated herein by reference.

Presented immediately below is an introductory summary of the general principles of modern optics relevant to the present invention. The summary is intended to provide context for a complete understanding of the invention. Those who are skilled in the art may proceed to the next section.

I. General Principles

When light travels from a first medium to a more optically dense second medium, the light is refracted toward the normal. Light approaching a rarefied medium from a dense medium is refracted away from the normal. There exists an angle, called the critical angle, $\theta_c$, such that for all angles of incidence greater than this angle, all of the light is reflected and none is transmitted. This effect is called total internal reflection (TIR) and occurs inside a material that is optically more dense than the material outside the boundary.

Figure 2:
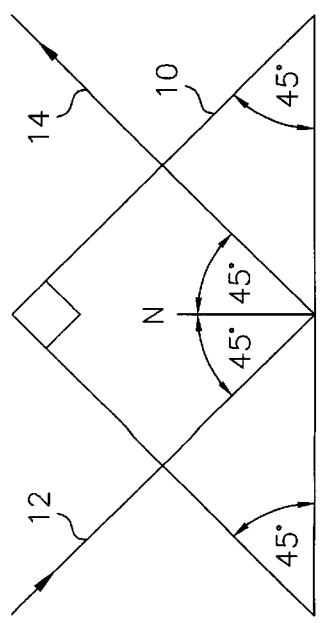
FIG. 2 illustrates total internal reflection in a prism.

A prism is one type of refractive and reflective device. As shown in FIG. 2, a prism 10 is a wedge of optical material that can either refract or totally reflect light, depending on the angle of incidence. The 45° glass prism shown in FIG. 2 is especially useful because incident light 12 entering normal to one face will totally reflect out the other face, having changed direction by 90°. Total reflection occurs because the light strikes the inner surface at 45°, which is greater than the critical angle of about 41° for glass. The line "N" represents a line normal (perpendicular) to a surface.

Figure 1:
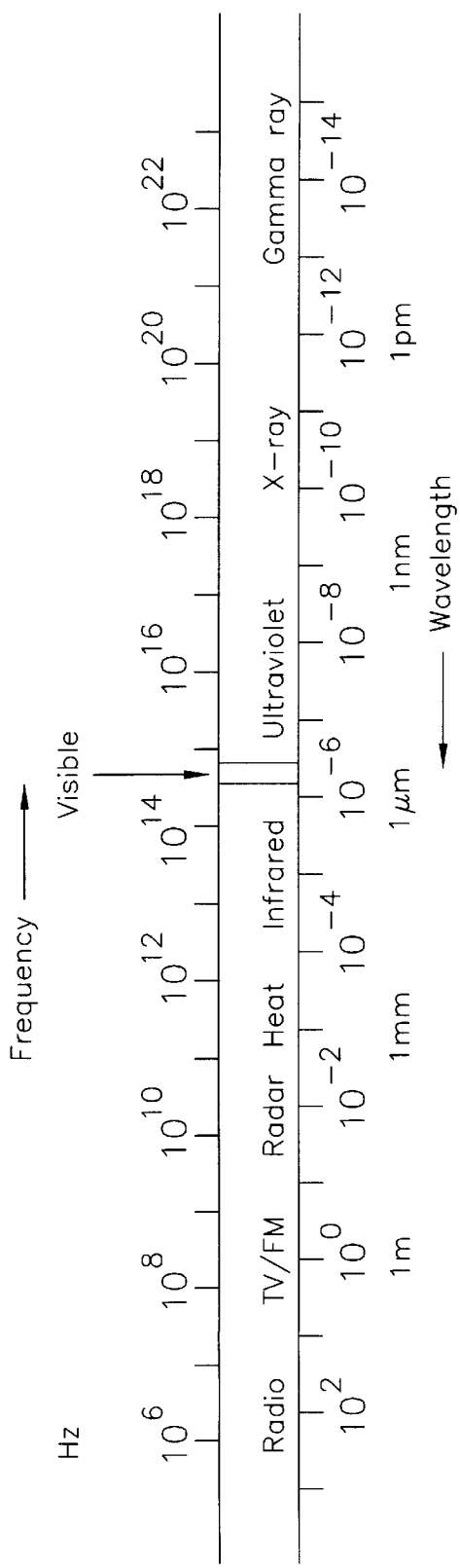
FIG. 1 illustrates the electromagnetic spectrum on a logarithmic scale.
Figure 3:
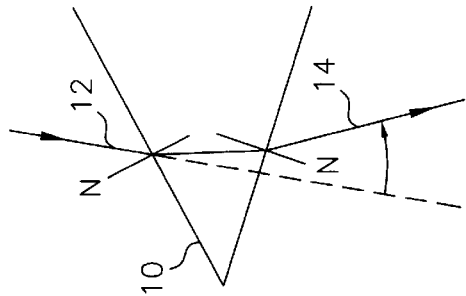
FIG. 3 illustrates deviation of light as it passes through a prism.
Figure 4:
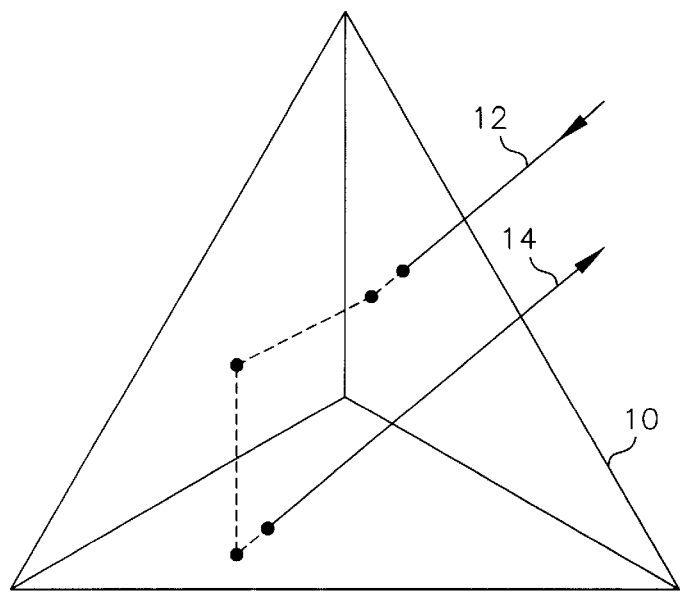
FIG. 4 illustrates how a corner reflector (retroreflector) returns light in exactly its original direction.

Light energy striking an outer surface of the prism 10 at an angle, shown in FIG. 3, is refracted in part, reflected in part by any internal surface, and refracted again as it emerges as exiting light 14. It has deviated from its original direction to emerge at a new angle. The general result is that the light is bent partly back in the direction from which it came. The deviation depends on the index of refraction of the prism, the angle of incidence, and on the angle in the vertex of the prism. For a symmetrical arrangement of incident and exiting light, 12 and 14 respectively, the angle of deviation is a minimum. More complex prisms use reflections to perform complex changes in image orientation. For example, the corner-cube prism 10 of FIG. 4 has the geometric property of sending light back exactly in the direction it came (i.e., to "retroreflect" the light).

Like all electromagnetic radiation, light is predicted by electromagnetic theory to be a transverse wave: the directions of the vibrating electric and magnetic vectors are at right angles to the direction of propagation (instead of parallel to it, as in a longitudinal wave). The transverse wave also has the characteristic that the vibrations of the electric vector are parallel to each other for all points in the wave (i.e., the wave is oriented, or polarized). In reality, incoherent (non-laser) light propagated in a given direction can consist of short, independent wavetrains whose planes of vibration are randomly oriented about the direction of propagation. Such light, although transverse, is unpolarized. Light can be partially or completely polarized by reflection.

Figure 5:
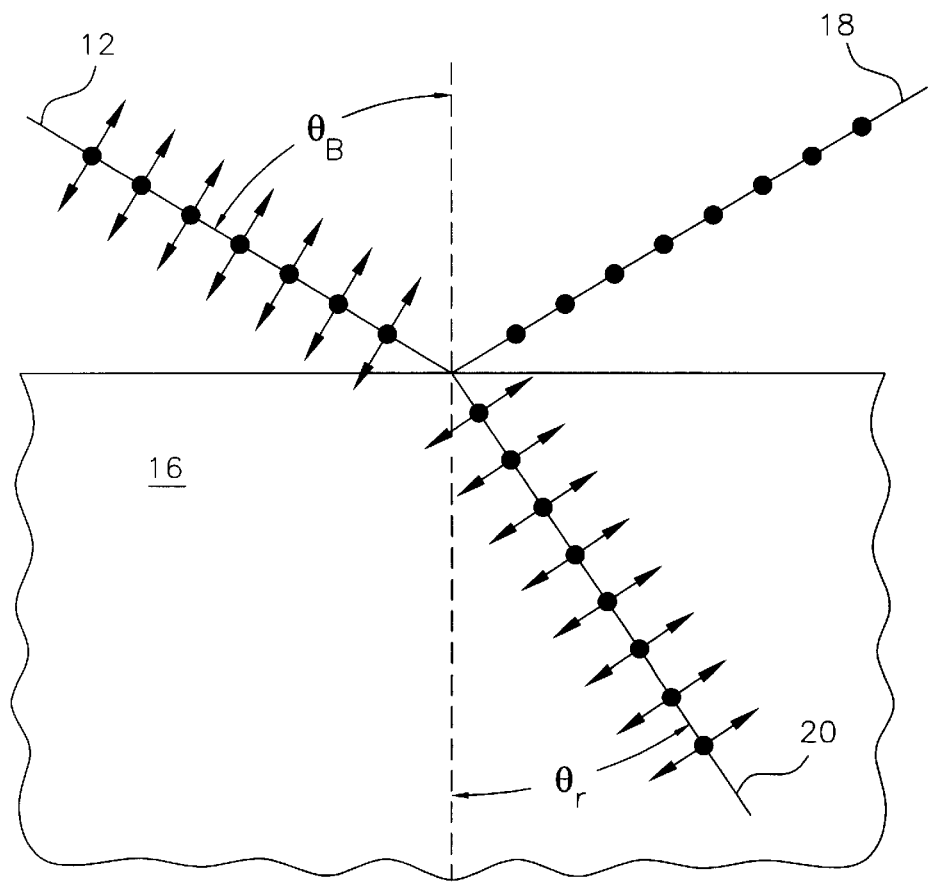
FIG. 5 illustrates an unpolarized light beam incident upon a glass surface.

FIG. 5 shows unpolarized incident light 12 traveling in air and falling on a glass surface 16. The glass has an index of refraction, n, of 1.5. The electric vector for each wavetrain in the light can be resolved into two components. One component is perpendicular to the plane of incidence, which is the plane of FIG. 5, and the other lies in the plane of incidence. The first component, represented by the dots, is the S-polarization component (from the German "senkrecht," meaning perpendicular). The second component, represented by the arrows, is the P-polarization component (for parallel). On average, for completely unpolarized light, these two components are of equal amplitude.

For glass or other dielectric materials, there is a particular angle of incidence, called the polarizing angle (also called Brewster's angle, $\theta_B$, because it was found experimentally by David Brewster), at which the reflection coefficient for the P-polarization component is zero. Thus, the light 18 reflected from the glass, although of low intensity, is plane-polarized, with its plane of vibration at right angles to the plane of incidence. The P-polarization component at the polarizing angle is entirely refracted at angle of refraction $\theta_r$; the S-polarization component is only partially refracted. Thus, the transmitted light 20, which is of high intensity, is only partially polarized.

Because light is a wave, it does not abruptly vanish on the other side of a boundary where there is total reflection. A damped non-propagating form of the wave leaks past and appears along the boundary as an "evanescent wave." This evanescent wave can be converted to a propagating wave if another surface is brought very close to the interface, within a few wavelengths. This process is called "frustrated total internal reflection."

Materials often are optically anisotropic in their response to light. In such materials, the response is different for the three independent directions possible in the material; in contrast, isotropic materials show no directional preference. For the purposes of this disclosure, materials are considered that have an identical response in two of the three directions. The third (unique) direction is referred to as the optic axis. In these materials, known as uniaxial, for light propagating in any direction except along the optic axis, the light can be resolved into two distinct waves with unique polarizations; one with the electric field oriented at right angles to the optic axis (the ordinary wave), and the other with a component of the electric field parallel to the optic axis (the extraordinary wave). These waves of different polarization refract differently in the medium, having different indices of refraction and, therefore, different speeds, which gives rise to a physical separation of the light and is referred to as double refraction or birefringence. Light that travels along the optic axis is always polarized at right angles to the axis and is purely an ordinary wave. In the more general case, with different response to light in the three spatial directions (biaxial systems), although more complex in analysis, a similar birefringence occurs. Common birefringent materials include calcite, crystalline quartz, and sapphire.

Figure 6:
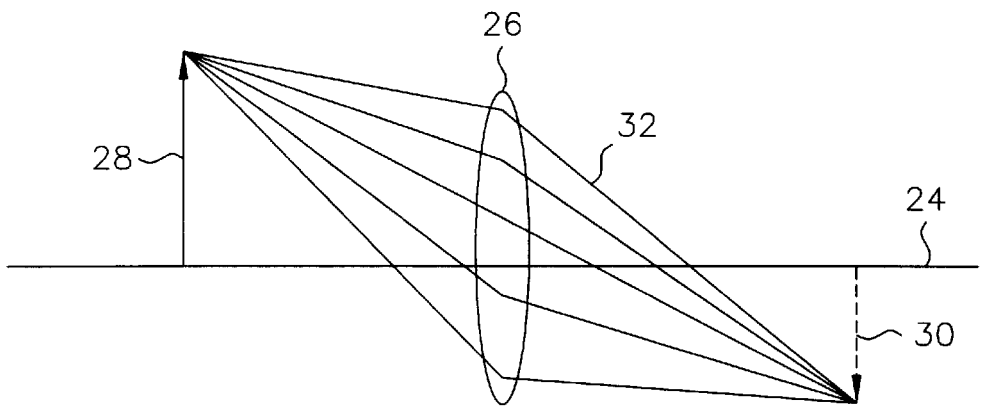
FIG. 6 is a side view of a lens, showing meridional rays and depicting how an off-axis object suffers astigmatism.
Figure 7:
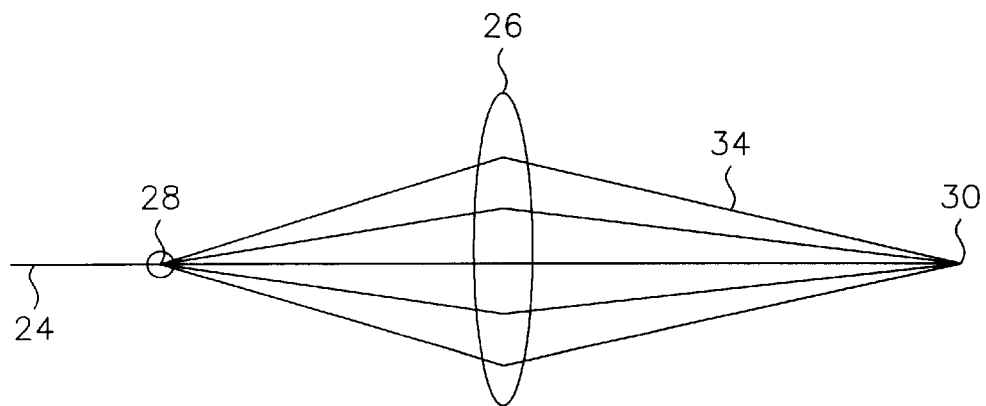
FIG. 7 is a top view of the lens shown in FIG. 6, showing sagittal rays and depicting how an off-axis object suffers astigmatism.

A lens 26 (disposed along axis 24 shown in FIGS. 6 and 7) maps each object point 28 into an image point 30. In astigmatism, the rays from off-axis object points arrive at different focal points. Consider the rays 32 from the top of the object shown in side view in FIG. 6. Rays 32 are in a meridional plane and pass through the lens 26 asymmetrically. Meanwhile, in the top view of lens 26 shown in FIG. 7, another set of rays 34 from the same point are in a sagittal plane and strike the lens 26 symmetrically. The focal points are separated for the two planes of rays, with the focal point for the sagittal rays 34 located a farther distance from lens 26 than for the meridional rays 32.

A simple way to test for astigmatism is to use a test pattern made of dots. In the two different focal planes, meridional and sagittal, there will be two different blurrings of the images of the pattern. In the meridional focal plane, the dots blur tangentially while in the sagittal focal plane the dots blur radially and form small arrows ("sagitta" is Latin for arrows) pointing toward the axis. This astigmatism occurs for spherically symmetrical lenses. These effects can be seen by this method only if the lens is free of other aberrations such as spherical and coma. Spherical aberration results in marginal rays being focused closer to the lens than axial rays; coma is an aberration where slanted rays have different focal points depending on which part of the lens they passed through.

II. The Resonator of the Present Invention

Figure 8:
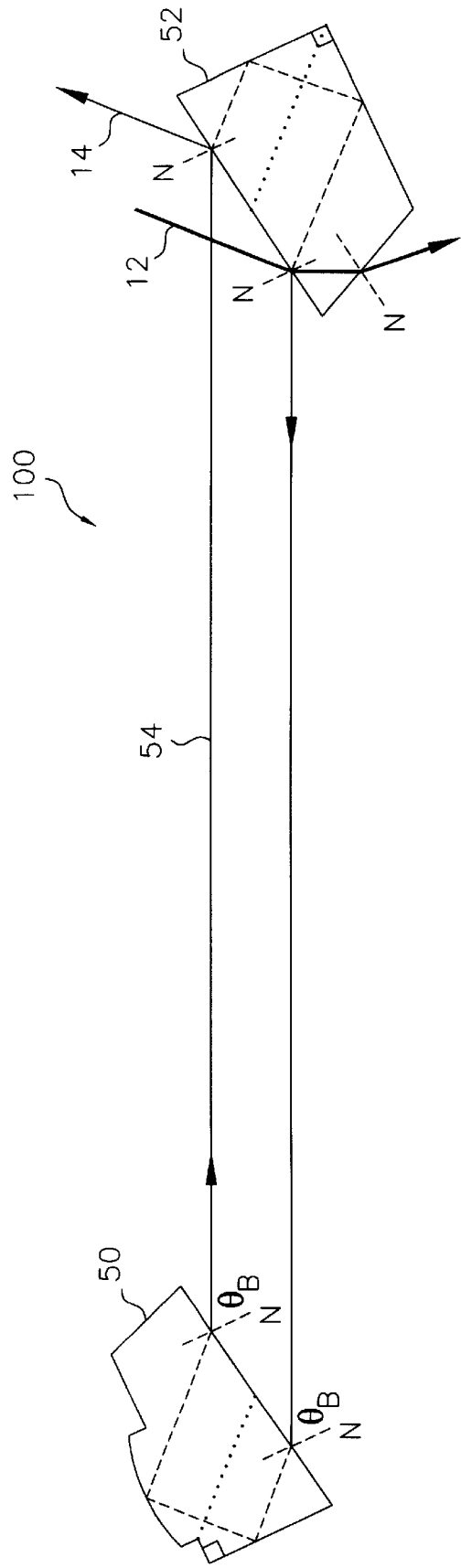
FIG. 8 illustrates the improved resonator for CRDS using two Brewster's angle retroreflector prisms.

The present invention provides an improved resonator 100 for CRDS based upon using two Brewster's angle retroreflector prisms 50, 52 made from a high quality optical material. FIG. 8 is a schematic drawing of prisms 50, 52; optic axis 54; and the expected optical path within each prism 50, 52. The polarizing or Brewster's angle, $\theta_B$, is shown relative to prism 50. The specific angles of FIG. 8 are drawn assuming that the prisms 50, 52 are made from fused silica, although (as will be discussed below) other materials could be used instead. Incident light 12 and exiting light 14 are illustrated as input to and output from prism 52, respectively. The resonant optical beam undergoes two total internal reflections without loss in each prism 50, 52 at about 45°, an angle which is greater than the critical angle for fused quartz and most other common optical prism materials.

Resonator optical losses are caused principally by (1) scattering due to imperfections and dirt at the surfaces of prisms 50, 52; (2) residual birefringence in the optical material, due to either strain or misalignment of the optic axis of the prism substrate material; (3) misalignment from parallelism of the coupling surfaces of the prisms 50, 52; (4) deviation from Brewster's angle; and (5) internal optical transmission loss in the prism substrates due to absorption or scattering. Prisms 50, 52 can be constructed to provide low loss (i.e., less than 0.01% per round trip) over a wide range of the optical spectrum. In addition, some of the most desirable materials for use as prism substrates, including but not limited to fused silica, sapphire, calcium fluoride, yttrium aluminum garnet, and diamond, are materials that are extremely hard and largely chemically inert, addressing the issue of hostile environments. Thus, resonator 100 for CRDS constructed from such prisms 50, 52 will meet and greatly expand the range of applicability of CRDS.

III. The Prism Design of the Present Invention

A preferred design of prisms 50, 52 is illustrated in FIGS. 9A and 9B. Taking it as an example, prism 52 has a first surface 1, a second surface 2, a third surface 3, and a fourth surface 4. FIG. 9A is a top view of prism 52 and shows the preferred length dimensions of surface 1 (25.8 mm), surface 2 (15 mm), and surface 3 (19 mm). FIG. 9B is a back view of prism 52 and shows the preferred height dimensions of surfaces 2, 3, and 4 (12.5 mm) and the preferred width of surfaces 3 and 4 combined (25.4 mm).

For prisms constructed of material with an index of refraction "n" relative to the surrounding medium (i.e., $n=n_2 \div n_1$, where $n_2$ is the index of refraction of the prism and $n_1$ is the index of refraction of the medium surrounding the prism—typically air with $n_1=1$), Brewster's angle, $\theta_B$, is given by the arctangent of n. The value of n for the example prism 52 shown in FIGS. 9A and 9B is about 1.4607; $\theta_B$ is about 55°36'. Prism 52 has a design center of about 0.532 $\mu$m. The apex angle of prism 52 ($\theta_1$) is set equal to 135°–$\theta_B$ and, in the preferred embodiment, is about 79°24'. Angle $\theta_2$ is preferably about 90°. Angle $\theta_3$ is set equal to 180°–2$\theta_B$ and, in the preferred embodiment, is about 68°48'.

Figure 10:
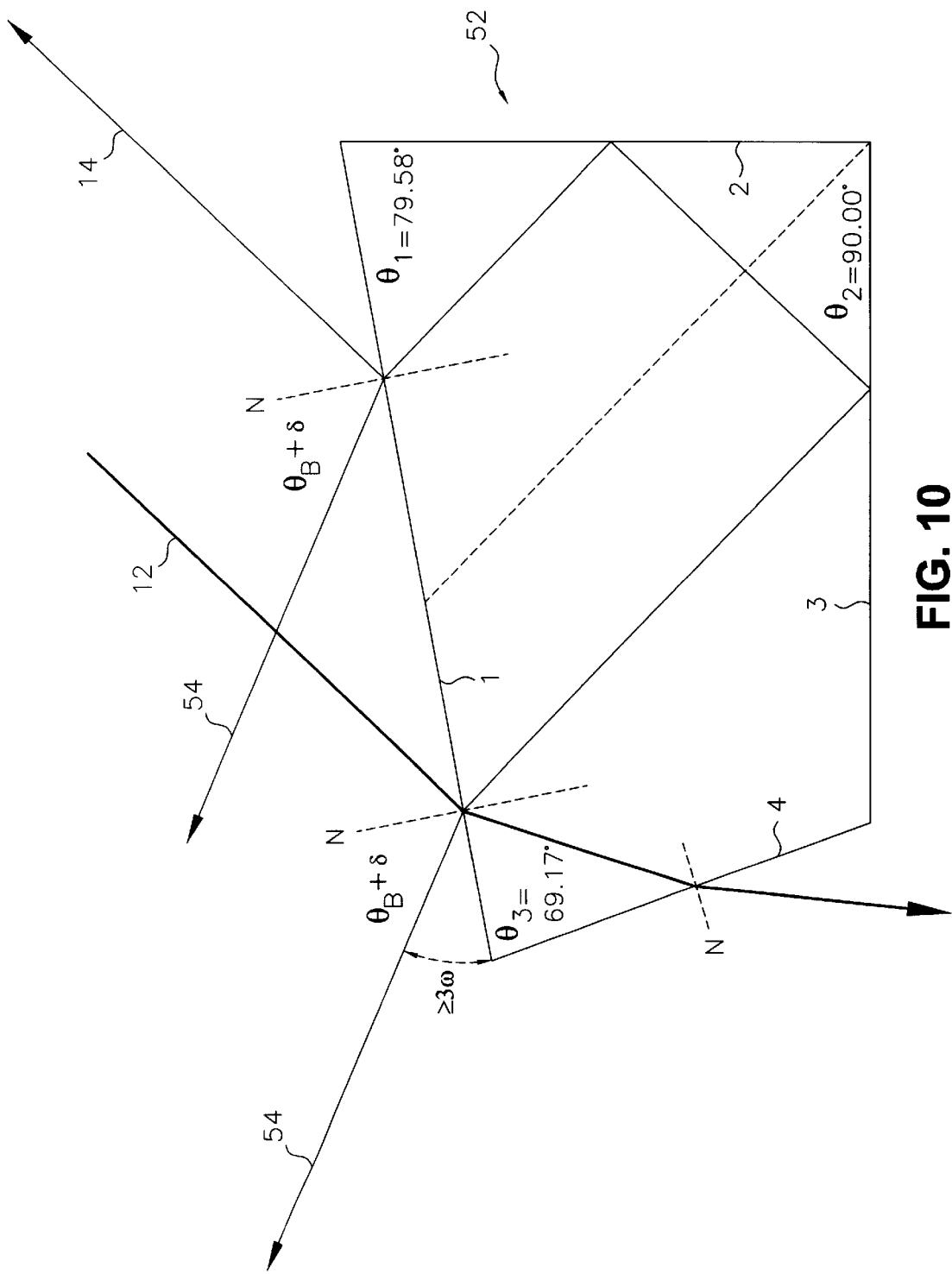
FIG. 10 shows how light incident rays enter and leave the prism nearly at Brewster's angle to the normal of the prism surface (with angles calculated for a prism made of fused silica)

FIG. 10 shows that rays of incident light 12 enter prism 52, and leave as rays of exiting light 14, nearly at Brewster's angle (within a small deviation, δ) to the normal "N" of surface 1. This results in small but controlled reflection loss for optical radiation with P-polarization with respect to the Brewster's angle surface. The value of n for the example prism 52 shown in FIG. 10 is approximately 1.45047; $\theta_B$ is about 55°25'. Prism 52 has a design center of 1 $\mu$m. Any optical radiation in the S-polarization is rapidly damped due to large reflection loss. The symbol "ω" characterizes the size of the spot generated by the light beam; negligible "clipping" of the beam occurs. The spot size for the lowest order mode can be calculated from standard optical resonator theory. For the prism 52 illustrated in FIG. 10, the apex angle ($\theta_1$) is preferably about 79°35' (or 79.58°). Angle $\theta_2$ is preferably about 90°. Angle $\theta_3$ is set equal to about 69°10' (or 69.17°).

IV. Material of Construction

The choice of optimal material for use in the construction of the prisms 50, 52 will depend upon the particular application. In order to allow for polishing of the surfaces to the required tolerances, a "hard" and chemically stable substrate material is needed. Also desirable is a material that has both low absorption and scattering loss over the spectral region of interest. Although five substrate materials are known to be suitable, namely fused silica, sapphire, calcium fluoride, yttrium aluminum garnet, and diamond, the present invention is not limited to these specific materials.

Fused silica is an excellent material which is widely used in the optics industry for construction of precision optical components. It has low absorption loss over a wide range of wavelengths. Because it is a glass, however, fused silica has frozen disorder on the molecular level that leads to significant Raleigh scattering loss, especially in the ultraviolet region.

Single crystal sapphire substrates are available and can also be manufactured to precision specifications. Sapphire has a wider spectral range of low absorption loss than fused silica; the highest quality samples have almost negligible scattering loss throughout the visible and into the near-ultraviolet region. Sapphire is a birefringent material and, to prevent excess loss due to polarization rotation within the resonator optics, the unique optic axis must be oriented along the axis perpendicular to the plane in FIG. 9A. This can be done to the required tolerance. The natural birefringence characteristic of sapphire is advantageous because the material is less susceptible to losses from strain birefringence which typically are the result of imperfect mechanical mounting of the prisms.

Sapphire is likely the material of choice for most applications. Diamond would in many ways be the ideal substrate material, except for the high cost of the material and processing.

V. Tuning

The use of "roof" retroreflectors renders a prism optical resonator alignment insensitive to small rotation of the prisms around the roof line and makes for a more robust alignment. Such a resonator can be constructed using Brewster's angle roof prisms with crossed axes. The advantage of this resonator is that it remains aligned for any small angle deviation of the prisms. The disadvantage is that the Brewster's angle of one of the prisms must be set by construction, i.e., it cannot be "tuned" by rotation of the prism around the roof axis. The resonator 100 of the present invention avoids that disadvantage.

Resonators can be characterized by a quality factor, Q, defined as the energy stored divided by the energy lost per cycle. Resonators with higher "Q" values are better at conserving energy and thus lead to higher sensitivity in cavity ring-down spectroscopy. According to the present invention, the resonator "Q" and coupling are controlled by tilting the prisms 50, 52 to adjust the level of reflection loss. The reflection loss per surface is determined by the Fresnel relations, and is approximately $10^{-4} \delta\theta^2$, where δθ is the deviation from Brewster's angle in degrees.

Light rays undergo two internal bounces at prism surfaces 2 and 3, and then leave the prism 50, 52 by transmission at surface 1. If angle $\theta_2$ is constructed to be 90°, the input rays or incident light 12 and output rays or exiting light 14 of the prism 50, 52 will be parallel but displaced if contained in the plane of FIG. 9A. The angles of incidence of both the rays of incident light 12 and the rays of exiting light 14 are equal, and can be tuned by rotation of the prism about the axis "R" normal to the plane in FIG. 9A. One approach to providing a mechanism for rotation of the prism is disclosed, in a generic sense, in FIG. 3 and at column 7, lines 14–30, of U.S. Pat. No. 5,483,343 issued to Rockwell. It is understood that the prisms 50, 52 have been aligned such that the roof lines forming the 90° angles are normal to the plane of FIG. 9A. As the prism 50, 52 is rotated, the angle of incidence for the internal reflections will increase by the same angle on one surface, and decrease by an equal amount on the other. In order to make these two total internal reflection angles approximately equal, the apex angle of the prism ($\theta_1$) should be constructed to be equal to $135°-\theta_B$.

For prisms made of fused quartz, Brewster's angle varies from 55.5–57.1° as the wavelength is varied from near-infrared to the onset of the vacuum ultraviolet (200 nm) while the critical angle varies from 43.4° to 40.31°. As a result, one pair of prisms 50, 52 can be designed to provide total internal reflection while allowing the tilt to reach Brewster's angle over that range of wavelength. By selecting angle $\theta_3$ to be equal to $180°-2\theta_B$, an optical beam coupled into the resonator by reflection from surface 1 will propagate through the crystal and also leave through surface 4 with an angle of incidence near Brewster's angle. This will reduce the amount of light energy that is reflected inside the prism that could be a source of unwanted stray light energy.

VI. Stability Control

Figure 11:
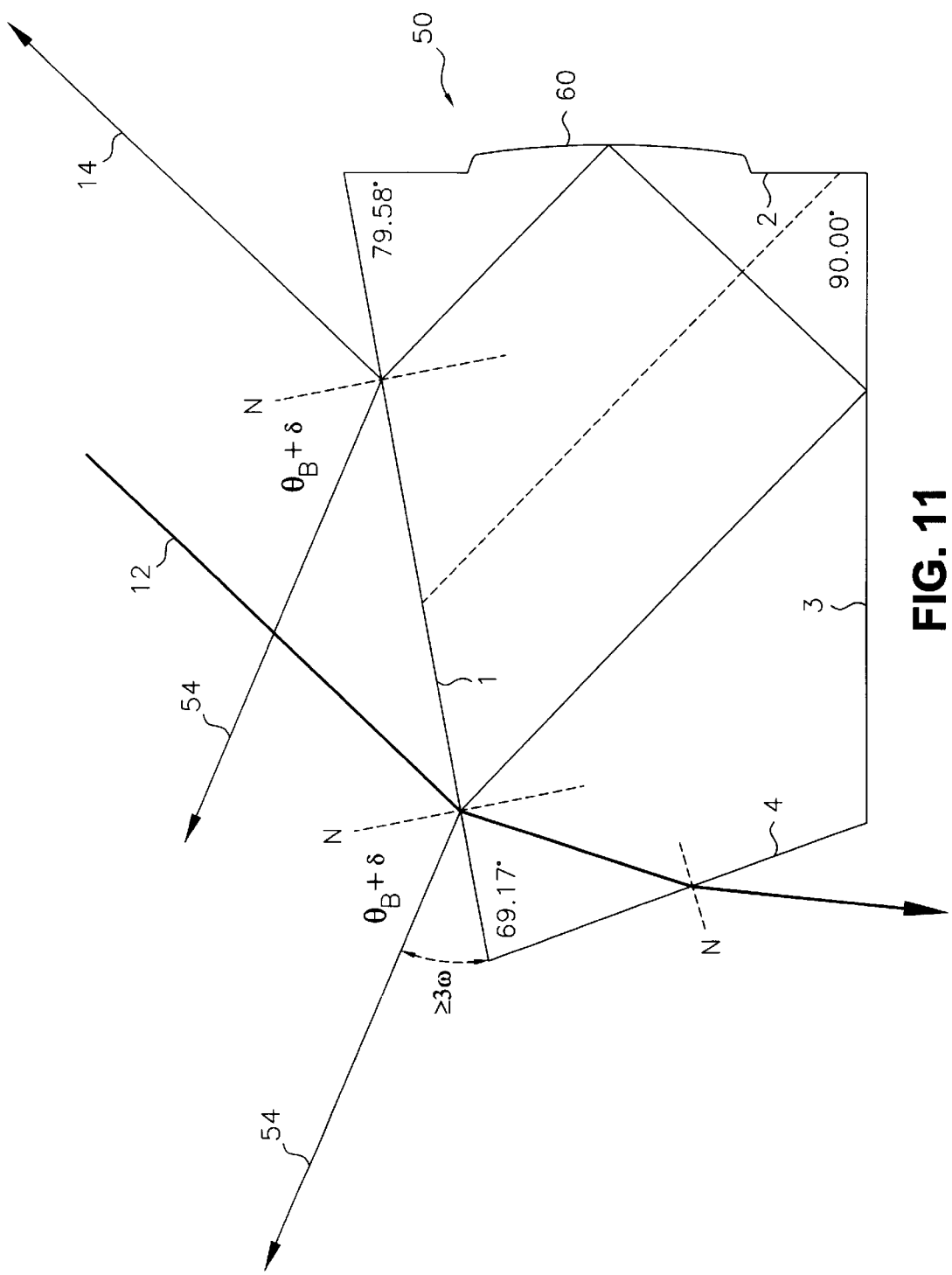
FIG. 11 depicts one of the total internal reflection surfaces on one prism ground with a curvature.

Optical resonator 100 is formed from a pair of prisms 50, 52 which act as retroreflectors. To form a stable optical resonator 100, and thus control the diffraction of the optical beam as it bounces back and forth, at least one of the total internal reflection surfaces on one prism is configured with a curvature. Such a curved surface 60 is shown in surface 2 of prism 50 in FIG. 11.

To correct for the astigmatism produced both by the Brewster's angle surface and reflection from the curved surface near 45°, the tangential curvature of curved surface 60 must be $2n^2\sqrt{2}f$ and the sagittal curvature (i.e., the curvature in the plane normal to that of FIG. 11) must be $\sqrt{2}f$, where f is the desired effective focal length of the curved surface 60. The focal length, f, is selected to be approximately equal to the separation distance between the two prisms, 50, 52, which is on the order of 1 meter in the preferred embodiment, to form a nearly half or folded confocal resonator 100.

Such an astigmatically compensated resonator 100 will have stable resonant modes that are cylindrical symmetric, simplifying the design of the mode-matching optics that are used to couple the radiation into the optical resonator 100. It will be appreciated that the construction of such a prism 50 may be difficult because it requires polishing and centering an astigmatic lens of precise curvature onto one of the prism surfaces. A simple spherical surface ground into one prism surface, such as surface 2, can be used with a curvature selected to give stability for rays with sagittal deviation from the optic axis 54 of the resonator. The presence of a focusing element inside the resonator 100 also compensates for small errors in the manufactured angles and the positioning of the prisms, 50, 52, maintaining stability and low loss despite diffraction and small deviations of the optic axis 54. In the latter case, the resonator eigenmodes will not be cylindrically symmetric.

Figure 12:
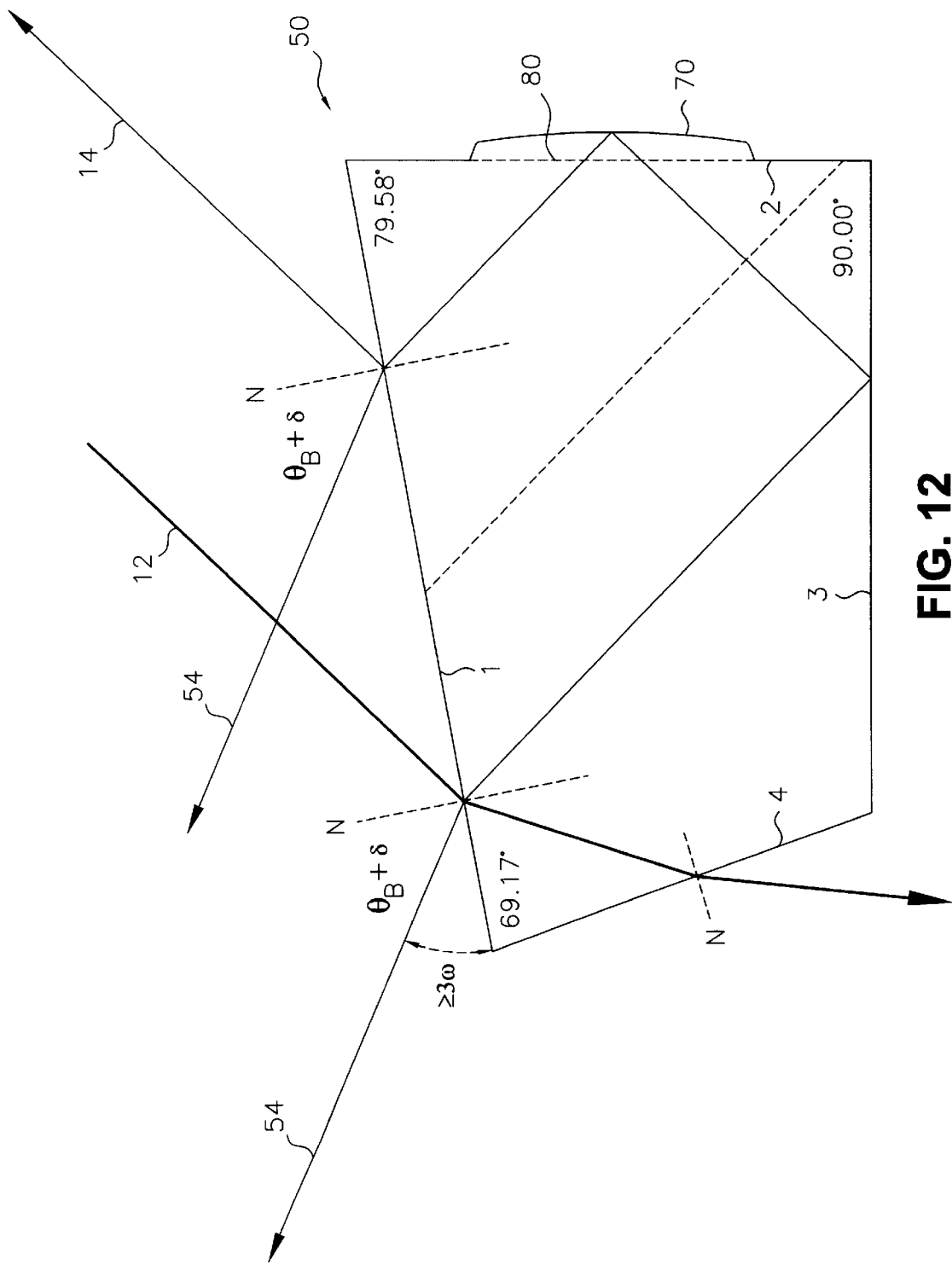
FIG. 12 shows a plano-convex lens optically contacted or glued to a prism surface.

Alternatively, as shown in FIG. 12, fabrication of prism 50 may be simplified by following a two step procedure. First, the prism 50 is fabricated with purely planar surfaces 1, 2, 3, and 4. Then a plano-convex lens 70 is made of the same material as prism 50 and of the appropriate astigmatism. The plano surface of the lens 70 is optically contacted to a prism surface (e.g., surface 2). When optically contacted, the interface between the components disappears, eliminating losses and providing optical performance equivalent to a monolithic (or integral, or one-piece) structure. When working with near-infrared and visible wavelengths, the lens 70 can be glued to the surface 2 of prism 50 with index-matching optical cement 80 which is a much simpler procedure than optical contacting.

Figure 13:
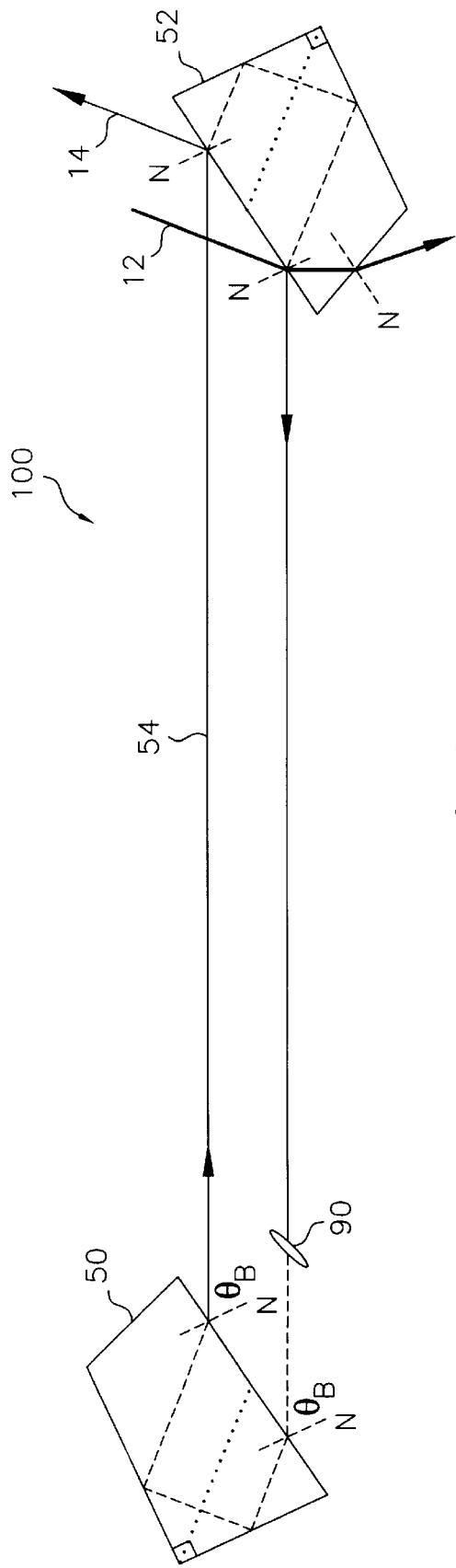
FIG. 13 illustrates a lens centered in one arm of the ring resonator, and tilted at Brewster's angle with respect to the optic axis.

An additional variation is, as shown in FIG. 13, to separate the lens completely from the body of either prism 50, 52. In this case, the astigmatic lens 90 is centered in one arm of the ring resonator 100 and tilted at Brewster's angle with respect to the optic axis 54, producing no reflection losses. The sagittal and tangential curvature are arranged to compensate for astigmatism while providing appropriate curvature for optical stability. As described below, the coupling is provided from one of the plano surfaces 1, 2, or 3 of the prisms 50, 52.

Radiation can be coupled into the resonator 100 in one of two ways. Frustrated total internal reflection can be used at one of the flat internal reflecting surfaces 2 or 3—or the prism 50, 52 can be tilted slightly away from Brewster's angle—to provide coupling from surface 1. The second method is technically easier but produces twice the loss for a given coupling parameter. The resonator 100 forms a ring and has no standing waves if light is coupled into it in one direction. Consequently, when one prism surface is rotated about its roof axis away from Brewster's angle to provide a means for coupling, the output from the same surface is spatially separated from the input, allowing for ease in separating the weak output beam from the intense input.

The use of a ring resonator 100 has certain additional advantages because it greatly reduces the level of optical radiation feedback to the source. Such feedback can potentially destabilize the source laser requiring the use of high precision optical isolators which themselves are of limited spectral bandwidth and add to overall system complexity and cost. The resonator 100 according to the present invention allows, for the first time, a broad bandwidth CRDS resonator to be constructed. Resonator 100 will clearly expand both scientific and commercial applications for CRDS spectroscopy. The broad spectral bandwidth of the improved CRDS resonator will allow for development of multispecies sensors.

VII. Prism Design with More than Two Internal Reflecting Surfaces

In FIGS. 8, 9A and 9B, a pair of right angle prisms 50, 52 with Brewster's angle interfaces constituted the reflective optics of the resonator 100. With that configuration, the angles of incidence at the two internally reflective surfaces of each prism 50, 52 were approximately 45°. For most materials that are useful for prisms, such as diamond and fused silica for example, that angle is sufficiently large to produce total internal reflection. For some optical materials in the infrared spectral region, however, such as calcium fluoride ($CaF_2$) for example, the index of refraction n is less $\sqrt{2}$ and, thus, too small to permit total reflection at such angles. Specifically, for $CaF_2$ the index of refraction is about 1.4093. Furthermore, there are situations, such as the immersion of the resonator 100 within a fluid, where the relative index of refraction of materials, such as fused silica and sapphire, would be reduced to a value that would make them unusable. For those situations, we consider altering the design of the prisms to permit radiation to strike the reflective surfaces at a greater angle of incidence.

For a pair prisms to operate properly, the light exiting the prism is preferably directed at approximately 180° (π radians) to the input direction. When a light ray reflects from a surface, the change in direction of the ray δ is given by equation (1):

$$\delta = 180° - 2\alpha, \quad (1)$$

where α is the angle of incidence.

For an arbitrary number of reflections m, at the same angle of incidence α, the change in direction $\delta_m$ is given by equation (2):

$$\delta_m = m \cdot (\pi - 2\alpha). \quad (2)$$

From this relation, by setting $\delta_m = \pi$ and solving for α, we find equation (3):

$$\alpha = (m-1)/m \cdot \pi/2 \quad (3)$$

From equation (3), it may be shown that, for a prism with two internal reflective surfaces, the angle of incidence α=π/4 (45°), and that by increasing the number of reflections within the prism, the angle of incidence α increases. Specifically, for three surfaces, α=60°, and for four surfaces, α=67.5°.

The critical angle $\theta_c$ is given by equation (4):

$$\theta_c = \sin^{-1}(1/n_r), \quad (4)$$

where $n_r$ is the relative index of refraction.

From equation (4) it is determined that, for three internal reflections, the relative index of refraction $n_r$ required for total reflection is 1.155, and for four internal reflections the relative index $n_r$ required for total reflection is 1.082. These values should be compared with $n_r$=1.414 ($\sqrt{2}$) for two internal reflections.

Therefore, by increasing the number of internal reflections, the scattering loss from the additional reflections is increased, degrading the performance of the resonator. According to the inventors, the most desirable configuration should minimize the number of internal reflections and still achieve total internal reflection.

There is a significant difference, however, between a prism designed with an even number of internal reflections and a prism designed with an odd number of internal reflections. In the case of an even number of internal reflections, small errors in the angle of incidence α are compensated in pairs, while this is not the case for an odd number of internal reflections. Thus, although a resonator constructed using a prism with three internal reflections is contemplated, it may have a limited tuning range and may require more precise construction. For this reason, a resonator according to a preferred embodiment of the present invention has an even number of internal reflections for each prism. Also, it should be noted that the angle of incidence α is not necessarily the same at each internal reflection.

In a preferred embodiment, the sum of all the angle changes due to internal reflections is π radians (180°), and the angles of incidence α each exceed the critical angle. The inventors have determined, however, that it is advantageous to make the various angles of incidence approximately equal to one another. Furthermore, when the angles of incidence for internal reflection are approximately equal to one another, the loss due to frustrated internal reflections is minimized. In addition, it is more cost effective and easier to construct such a prism since many of the facets will have the same angle. In fact, in the preferred embodiment, the number of facets having the same angles will be one less that the number of internal reflections.

Figure 14:
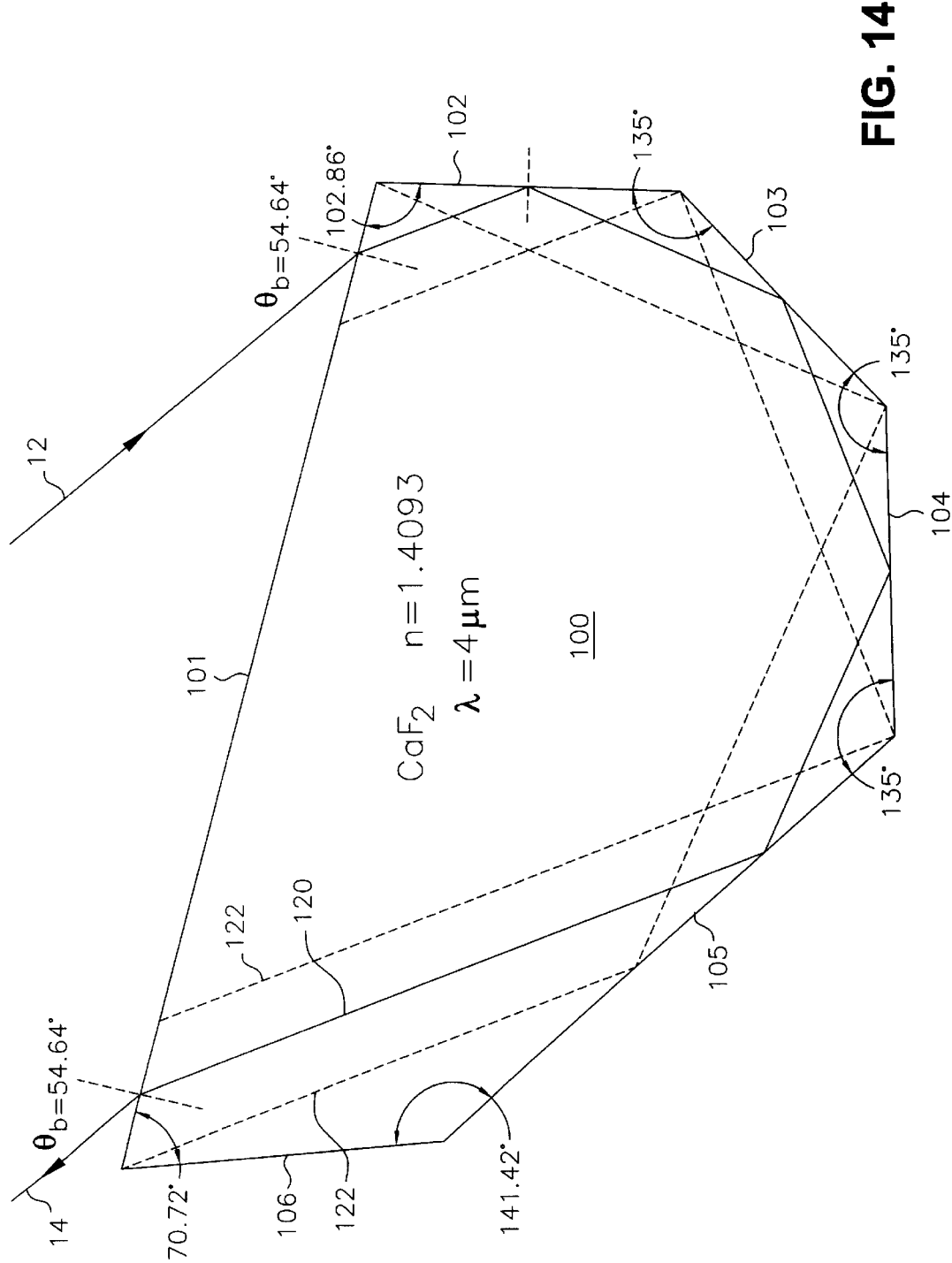
FIG. 14 is an illustration of a prism having more than two internal reflecting surfaces according to an embodiment of the present invention.

Referring now to FIG. 14, an exemplary Brewster's prism 100 with four internal reflections is shown. In this exemplary embodiment, the number of internal reflections is four, although, as discussed above, a prism having three or more internal reflections is also contemplated and within the scope of the present invention.

Figure 15:
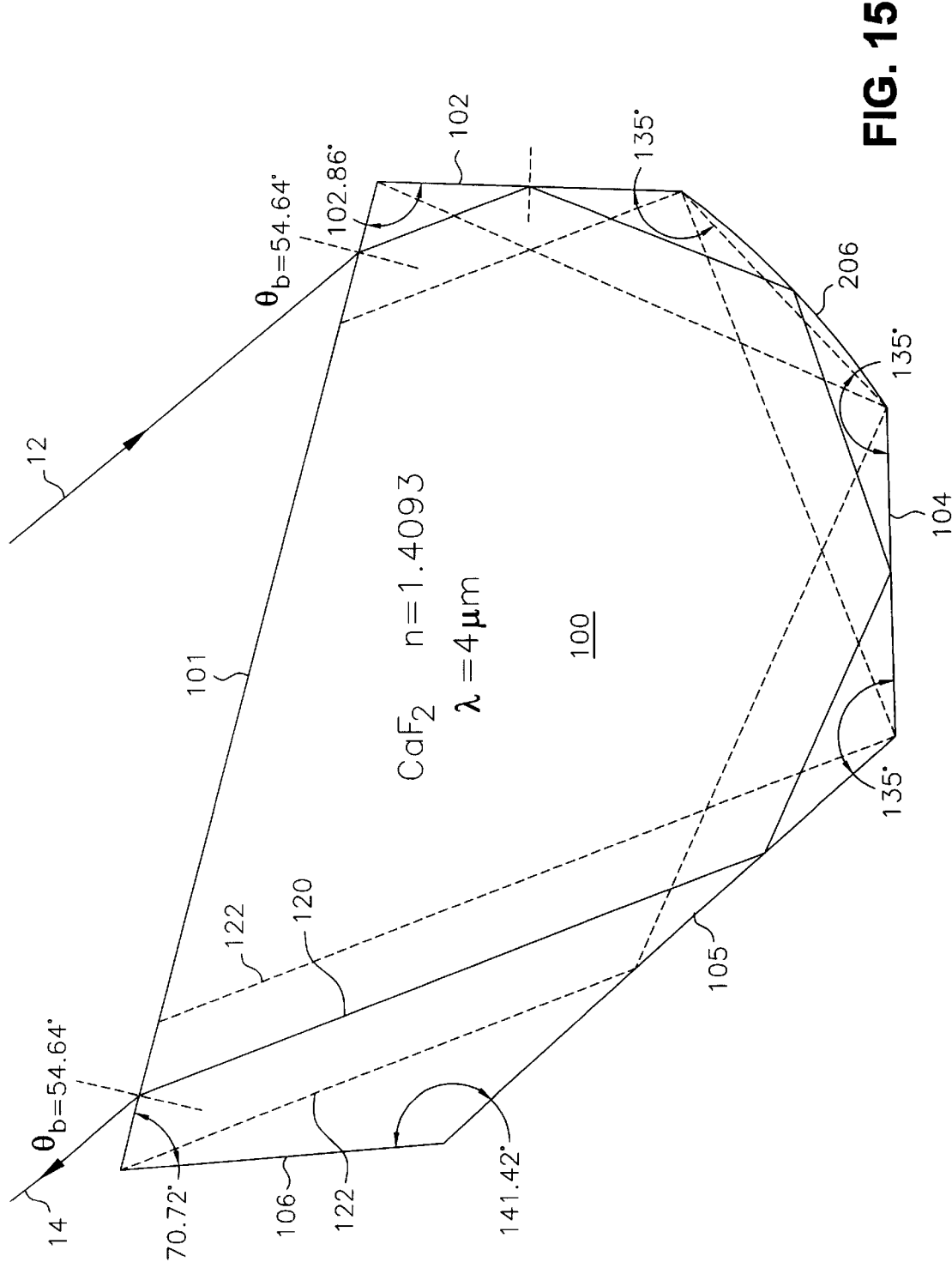
FIG. 15 is an illustration of a prism having more than two internal reflecting surfaces including a curved surface according to a further embodiment of the present invention.

In FIG. 14, solid line 120 represents the central ray of the radiation 12 incident on surface 101 of prism 100 at about Brewster's angle. The dashed lines 122 represent the rays of radiation 12 at approximately twice the spot size, 2ω. In the exemplary embodiment of FIG. 14, the material of prism 100 is preferably calcium fluoride, and the angles shown are for an exemplary central wavelength of 4.0 μm. As shown in FIG. 14, prism 100 has 6 surfaces 101–106, inclusive. It is also contemplated that a curved face 206, shown in FIG. 15, providing positive optical power may be included in prism 100 in order to make the resonator stable. The curved face 206 may be part of prism 100 or a separate lens attached to a face 103 of prism 100, similar to the exemplary embodiments discussed above.

Figure 16:
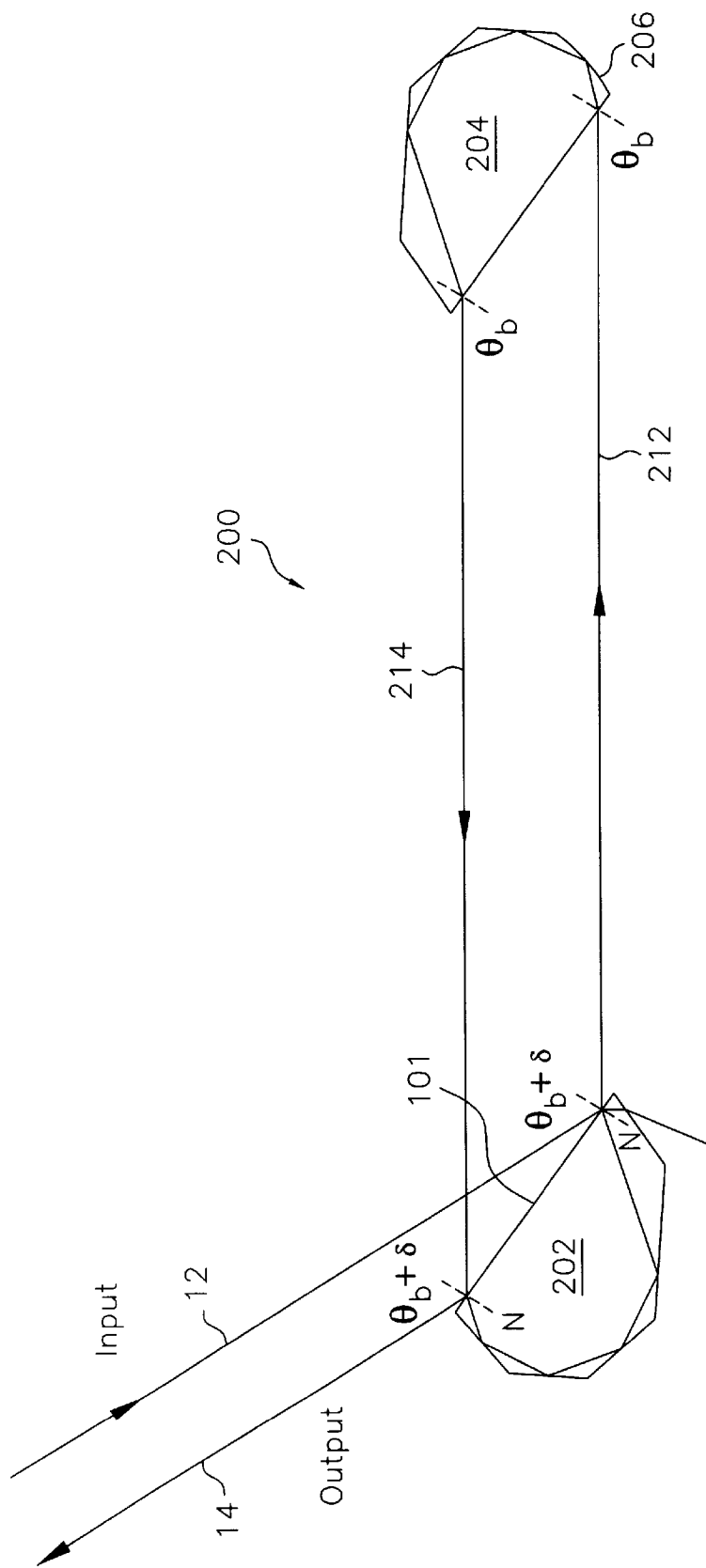
FIG. 16 illustrates an embodiment of a CRDS using a prism of FIG. 14 and a prism of FIG. 15.

Referring now to FIG. 16, an exemplary resonator 200 is shown. In FIG. 16, resonator 200 includes prisms 202, 204 each having greater than two internal reflective surfaces. Incident light 12 and exiting light 14 are illustrated as input to and output from prism 202, respectively. In the exemplary resonator 200 of FIG. 16, the resonant optical beam undergoes four total internal reflections without loss in each prism 202, 204 at an angle which is greater than the critical angle for the exemplary material Calcium fluoride. Radiation 12 in the p-polarization is incident on prism 202 at surface 101 and reflected into resonator 200 at an angle close to Brewster's angle $\theta_B$. Radiation 212 is transmitted to prism 204 and undergoes four total internal reflections. Radiation 214 is returned from prism 204 and is incident on surface 101 of prism 202 at nearly Brewster's angle $\theta_B$. For purposes of simplicity, it is assumed that the angle of incidence is equal to Brewster's angle. In the exemplary embodiment of FIG. 16, curved surface 206 replaces planar surface 106. It is understood, however, that resonator 200 may be constructed with prisms having only planar surfaces, such as shown in FIG. 14, if desired, including other means for optical stability, such as lens 90 shown in FIG. 13.

Figure 17:
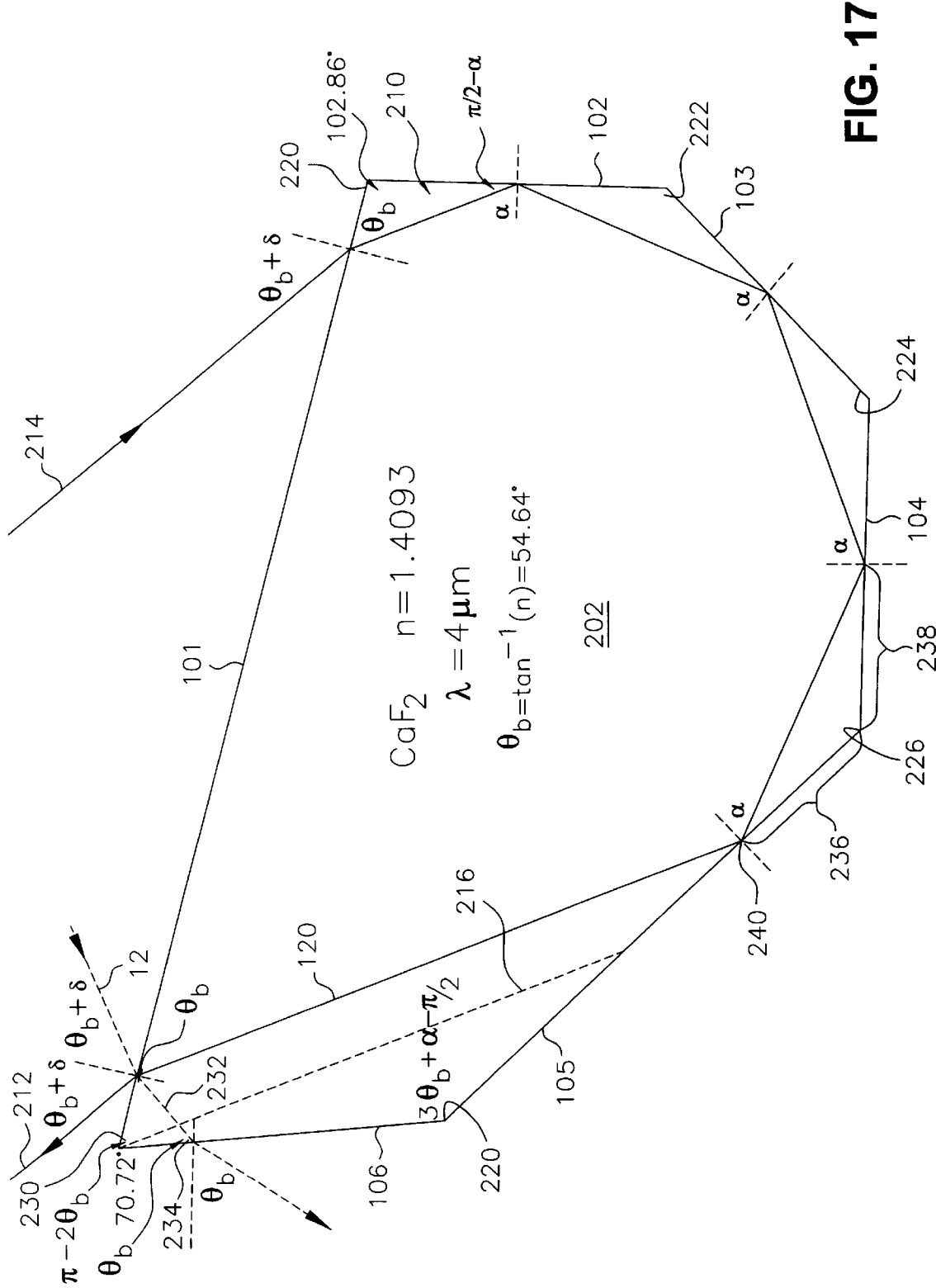
FIG. 17 is a detailed illustration of the angles and facets of the prism of FIG. 14.

Referring to FIG. 17, prism 202 is shown in greater detail. Tracing the beam 214 using Snell's law, $n_i \sin \theta_i = n_r \sin \theta_r$ (where i and r refer to the incident and refracted beams, respectively, and n is the index of refraction, of the respective media), the angle that the refracted ray makes with the normal to the Brewster surface is determined to be the compliment of Brewster's angle, that is about 35.36°. Beam 214 strikes each of surfaces 102, 103, 104 and 105 successively at an angle of incidence α, which according to equation (3) above is about 67.5°.

The internal angles of prism 202 may now be determined according to Euclidean geometry. For example, the triangle 210 formed by i) beam 214, ii) surface 101 and iii) the first reflecting surface 102, has two known angles, $\theta_B$ and (π/2−α). Therefore, the unknown angle 220 is found to be about 102.86°. Following this approach, the remaining internal angles 222, 224, 226 of prism 202 may also be determined. In the exemplary embodiment these angles are each about 2α (about 135°).

Ordinarily, following this approach, a fifth surface 216 (shown in phantom in FIG. 17) would complete the prism 202. This is not a desired result, however, because the majority of radiation (of no direct use) 232 is transmitted through the prism 202 and, in general, will reflect from surface 216 and scatter light throughout prism 202. By adding a sixth surface 106, as shown in FIG. 16, the extraneous radiation will be incident at nearly Brewster's angle 234 and exit at surface 106, resulting in greatly reduced reflectivity. Furthermore, the central ray 120 should preferably strike the approximate center of the first three reflecting surfaces 102, 103, 104, and at a point 240 on surface 105 having a distance 236 measured from apex 226 (adjacent surfaces 104 and 105) at least as great as the distance 238. It is also preferable that the length of the first three surfaces 102, 103, 104 be approximately equal to one another and the length of the surface 105 is longer than the length of any of the first three surfaces 102, 103, 104. The angles of the triangle formed by the dashed line 216, facet 106, and part of facet 105, are now obtained using Euclidean geometry. In particular, angle 228 is $3\theta_B + \alpha - 90°$, or about 141.42°, thus, defining all the angles formed by the facets of prism 202.

The overall size of the prism 202 and the length of each side 102, 103, 104, 105, 106 is chosen so that a beam 12 of a given spot size $\omega$ is not obscured, resulting in a large loss. Furthermore, it is desirable that the diffraction loss is selected to be less than the scattering loss of the prism 202. Referring again to FIG. 14, the relation between the spot size $\omega$ and the dimensions of prism 100 are shown by 122 which represent the laser field at a distance of about $2\omega$ from the beam center.

Figure 18:
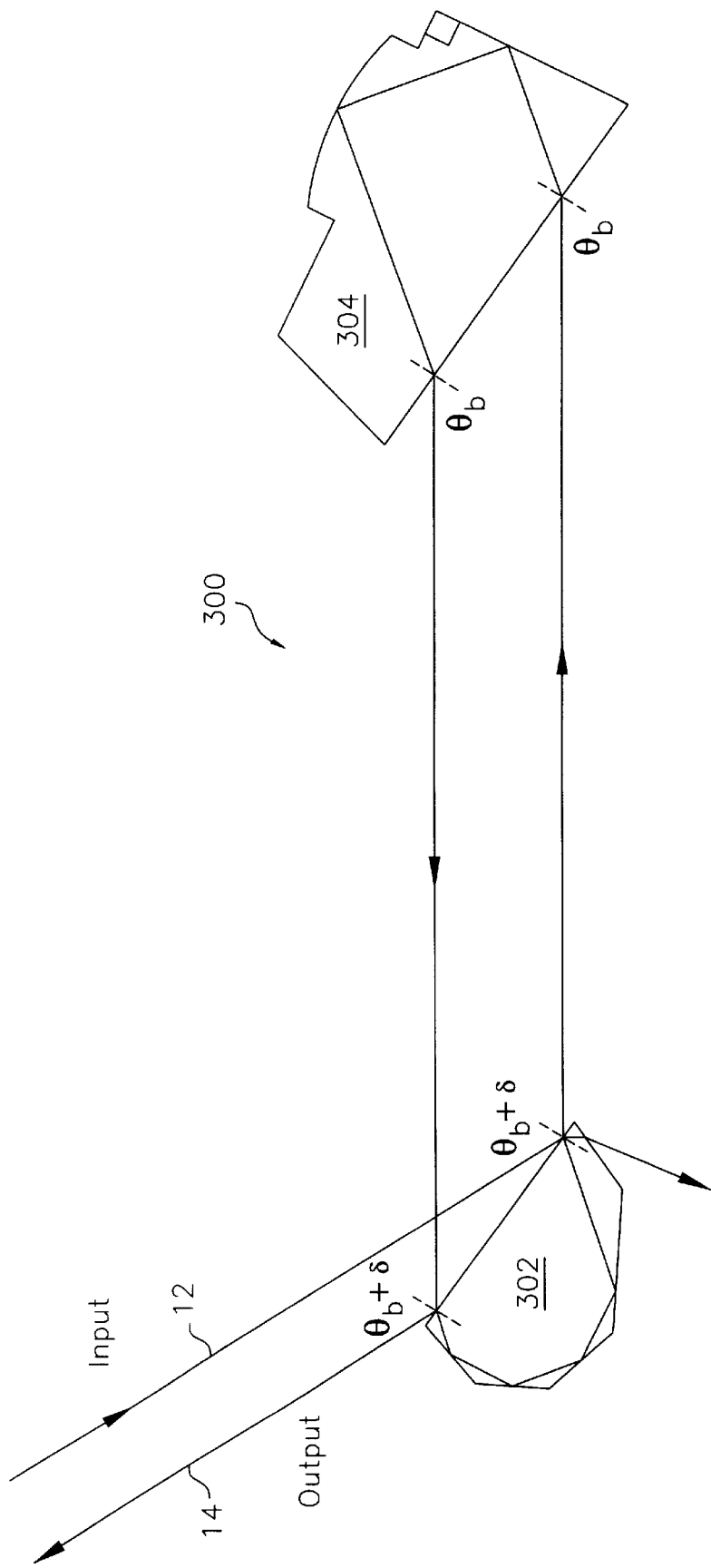
FIG. 18 illustrates another embodiment of a CRDS using two prisms of FIGS. 11 or 12, and FIG. 16, respectively.

Although, in the exemplary embodiment of FIG. 16, two prisms having more than two internal reflecting surfaces are included in resonator 200, the present invention is not so restricted. Another exemplary embodiment of the present invention is shown in FIG. 18. In FIG. 18, resonator 300 includes a prism 302 similar to prism 202 (shown in FIG. 16) and a prism 304 similar to prism 50 (shown in either FIGS. 11 or 12). All other aspects of this embodiment, including the determination of angles and lengths of prism surfaces, have been discussed above with respect to the other exemplary embodiments and, therefore, are not repeated.

Figure 19:
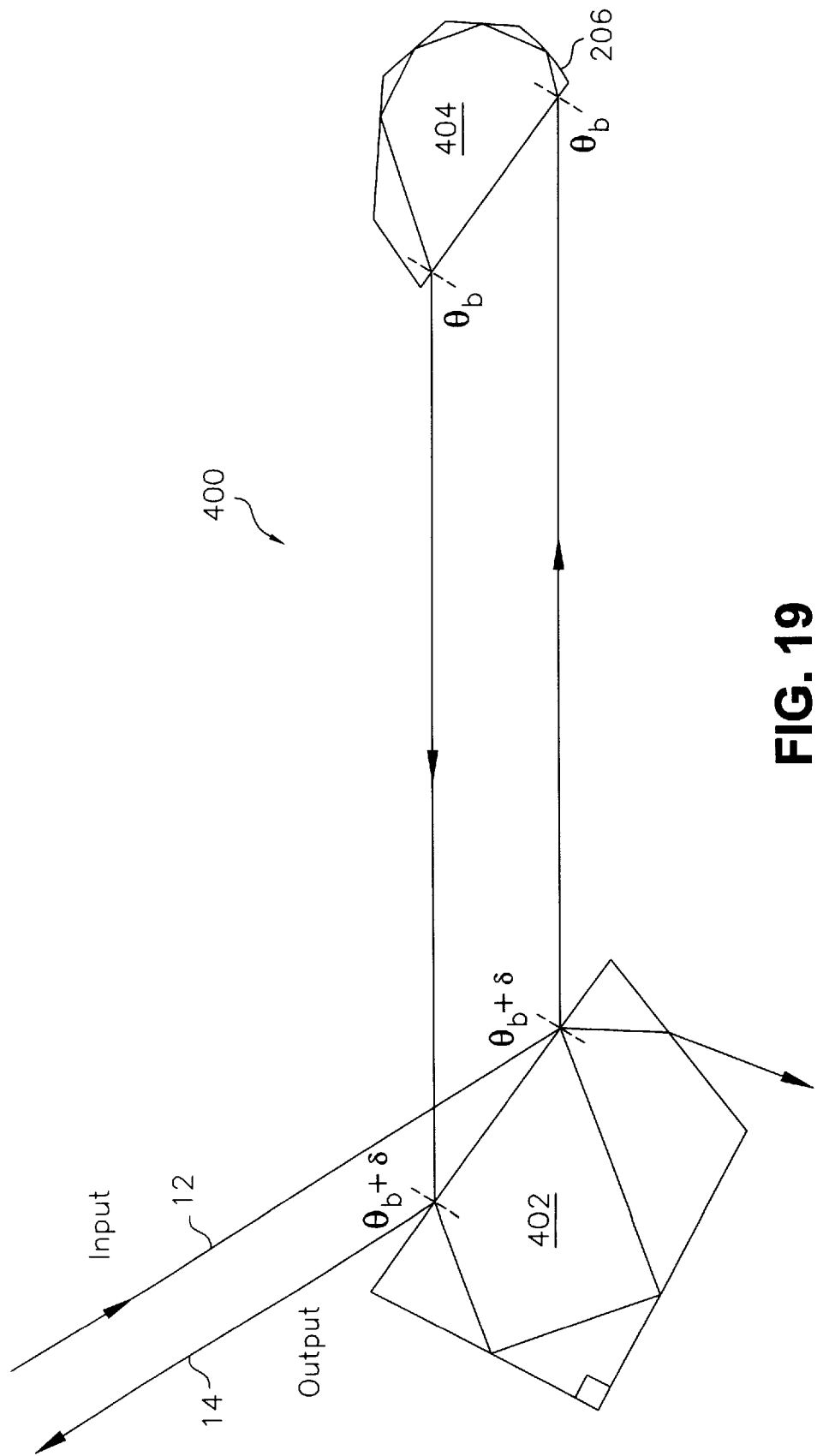
FIG. 19 illustrates another embodiment of a CRDS using prisms of FIGS. 10 and 16, respectively.

Yet another exemplary embodiment of the present invention is shown in FIG. 19. In FIG. 19, resonator 400 includes a prism 402 similar to prism 52 (shown in FIG. 10) and a prism 404 similar to prism 204 (shown in FIG. 16). With respect to these last two embodiments, it should be noted that the prisms 304 and 402 are of a size sufficiently large to match the output rays of the complimentary prism 302 and 404, respectively, so that the rays are incident on the prism at about Brewster's angle.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A stable resonator for a ring-down cavity spectroscopy cell having an optic axis, the resonator comprising:
    a first Brewster's angle retroreflector prism having greater than two total internal reflection surfaces; and
    a second Brewster's angle retroreflector prism having a plurality of total internal reflection surfaces and being disposed in alignment with the first prism along the optic axis of the resonator;
    wherein radiation enters and leaves a surface of the one of the prisms nearly at Brewster's angle to the normal of the prism surface, and a relative index of refraction of at least one of the prisms is less than about $\sqrt{2}$.

2. The resonator as recited in claim 1, wherein at least one of the prisms is rotatable to at least i) maintain alignment between the prisms or ii) tune the resonator.

3. The resonator as recited in claim 2, wherein both of the prisms are rotatable.

4. The resonator as recited in claim 1, wherein the prisms are formed from at least one of fused silica, sapphire, diamond, calcium fluoride, and yttrium aluminum garnet.

5. The resonator as recited in claim 1, wherein the first prism has one internal angle of about 180° minus twice Brewster's angle, a second internal angle of about 90° plus an angle of incidence minus Brewster's angle, and a third internal angle of about three times Brewster's angle plus the angle of incidence minus 90°, the angle of incidence based on a number of total internal reflection surfaces of the first prism.

6. The resonator as recited in claim 5, wherein the number of total internal reflection surfaces of the first prism is four, and the angle of incidence is about 67.5°.

7. The resonator as recited in claim 1 wherein one of the total internal reflection surfaces of at least one of the prisms is a curved surface.

8. The resonator as recited in claim 7, wherein a tangential curvature of the curved surface is $2n^2 f / \cos \alpha$ and a sagittal curvature of the curved surface is $2f \cos \alpha$, where f is the effective focal length of the curved surface and n is the index of refraction of the at least one prism.

9. The resonator as recited in claim 1, further comprising a lens of the same material as the first prism and having a planar surface and a convex surface, the planar surface of the lens engaging one of the total internal reflection surfaces of the first prism.

10. The resonator as recited in claim 9, wherein the lens optically contacts the engaged total internal reflection surface of the first prism.

11. The resonator as recited in claim 9, further comprising an optical cement, the optical cement gluing the lens to the engaged total internal reflection surface of the first prism.

12. The resonator as recited in claim 1, wherein the radiation enters and leaves the surface of the first prism nearly at Brewster's angle to the normal of the surface of the first prism.

13. The resonator as recited in claim 1, wherein the radiation enters and leaves the surface of the second prism nearly at Brewster's angle to the normal of the surface of the second prism.

14. The resonator as recited in claim 1, further comprising a plurality of surfaces, at least two of the plurality of surfaces having a length about equal to one another.

15. The resonator as recited in claim 14, wherein the plurality of surfaces includes at least three surfaces and the length of three of the plurality of surfaces are about equal to one another.

16. A resonator for a ring-down cavity spectroscopy cell having an optic axis, the resonator comprising:
    a first Brewster's angle retroreflector prism having greater than two total internal reflection surfaces with one of the total internal reflection surfaces being a curved surface;
    a second Brewster's angle retroreflector prism having a plurality of total internal reflection surfaces and being disposed in alignment with the first prism along the optic axis of the resonator; and means for independently rotating each of the prisms so that radiation enters and leaves a surface of each prism nearly at Brewster's angle to the normal of the prism surface, wherein alignment between the prisms is maintained and the resonator is tuned.

17. The resonator as recited in claim 16, wherein the prisms are one of fused silica, sapphire, diamond, calcium fluoride, and yttrium aluminum garnet.

18. The resonator as recited in claim 16, wherein at least one of the prisms has one internal angle of about 180° minus twice Brewster's angle, a second internal angle of about 90° plus an angle of incidence for internal reflection minus Brewster's angle, and a third internal angle of about three times Brewster's angle plus the angle of incidence for internal reflection minus 90°, the angle of incidence based on a number of total internal reflection surfaces of the first prism.

19. The resonator as recited in claim 16, wherein a tangential curvature of the curved surface is $2n^2f/\cos\alpha$ and a sagittal curvature of the curved surface is $2f\cos\alpha$, where f is the effective focal length of the curved surface and n is the index of refraction.

20. The resonator as recited in claim 16, wherein an index of refraction of at least one of the prisms is less than about $\sqrt{2}$.

21. A resonator for a ring-down cavity spectroscopy cell having an optic axis, the resonator comprising:
   a first Brewster's angle retroreflector prism having:
      (a) greater than two total internal reflection surfaces with one of the total internal reflection surfaces being a curved surface,
      (b) an apex angle of about 180° minus twice Brewster's angle,
      (c) a second angle of about 90° plus an angle of incidence minus Brewster's angle, and
      (d) a third angle of about three times Brewster's angle plus the angle of incidence minus 90°;
   a second Brewster's angle retroreflector prism having a plurality of total internal reflection surfaces and being disposed in alignment with the first prism along the optic axis of the resonator; and
   at least one of the prisms being rotatable so that radiation enters and leaves a surface of the prism nearly at Brewster's angle to the normal of the prism surface, wherein alignment between the prisms is maintained and the resonator is tuned.

22. The resonator as recited in claim 21, wherein both of the prisms are rotatable.

23. The resonator as recited in claim 21, wherein the prisms are formed from at least one of fused silica, sapphire, diamond, calcium fluoride, and yttrium aluminum garnet.

24. The resonator as recited in claim 21, wherein the first prism is fused calcium fluoride, the apex angle is between about 101–103°, the second angle is between about 70–71°, and the third angle is between about 141–142°.

25. The resonator as recited in claim 21, wherein a tangential curvature of the curved surface is $2n^2f/\cos\alpha$ and a sagittal curvature of the curved surface is $2f\cos\alpha$, where f is the effective focal length of the curved surface and n is the index of refraction.

26. The resonator as recited in claim 21, wherein an index of refraction of at least one of the prisms is less than about $\sqrt{2}$.

27. A stable resonator for a ring-down cavity spectroscopy cell having an optic axis, the resonator comprising:
   a first Brewster's angle retroreflector prism having greater than two total internal reflection surfaces; and
   a second Brewster's angle retroreflector prism having greater than two total internal reflection surfaces and being disposed in alignment with the first prism along the optic axis of the resonator;
   wherein radiation enters and leaves a surface of the one of the prisms nearly at Brewster's angle to the normal of the prism surface.

28. The resonator as recited in claim 27, wherein a number of the total internal reflection surfaces of at least one of the prisms is an even quantity.

29. The resonator as recited in claim 27, wherein an index of refraction of at least one of the prisms is less than about $\sqrt{2}$.

30. A stable resonator for a ring-down cavity spectroscopy cell having an optic axis, the resonator comprising:
   a first Brewster's angle retroreflector prism having i) greater than two total internal reflection surfaces, ii) one internal angle of about 180° minus twice Brewster's angle, iii) a second internal angle of about 90° plus an angle of incidence for internal reflection minus Brewster's angle, and iv) a third internal angle of about three times Brewster's angle plus the angle of incidence for internal reflection minus 90°, the angle of incidence based on a number of total internal reflection surfaces of the first prism; and
   a second Brewster's angle retroreflector prism having a plurality of total internal reflection surfaces and being disposed in alignment with the first prism along the optic axis of the resonator;
   wherein radiation enters and leaves a surface of the one of the prisms nearly at Brewster's angle to the normal of the prism surface.

31. A stable resonator for a ring-down cavity spectroscopy cell having an optic axis, the resonator comprising:
   a first Brewster's angle retroreflector prism having greater than two total internal reflection surfaces; and
   a second Brewster's angle retroreflector prism having a plurality of total internal reflection surfaces and being disposed in alignment with the first prism along the optic axis of the resonator;
   wherein radiation enters and leaves a surface of the one of the prisms nearly at Brewster's angle to the normal of the prism surface, and one of the total internal reflection surfaces of at least one of the prisms is a curved surface.

32. A stable resonator for a ring-down cavity spectroscopy cell having an optic axis, the resonator comprising:
   a first Brewster's angle retroreflector prism having greater than two total internal reflection surfaces;
   a second Brewster's angle retroreflector prism having a plurality of total internal reflection surfaces and being disposed in alignment with the first prism along the optic axis of the resonator; and
   a lens of the same material as the first prism and having a planar surface and a convex surface, the planar surface of the lens engaging one of the total internal reflection surfaces of the first prism;
   wherein radiation enters and leaves a surface of the one of the prisms nearly at Brewster's angle to the normal of the prism surface.

33. A stable resonator for a ring-down cavity spectroscopy cell having an optic axis, the resonator comprising:
   a first Brewster's angle retroreflector prism having greater than two total internal reflection surfaces; and
   a second Brewster's angle retroreflector prism having a plurality of total internal reflection surfaces and being disposed in alignment with the first prism along the optic axis of the resonator;

wherein radiation enters and leaves a surface of the second prism nearly at Brewster's angle to the normal of the surface of the second prism.

34. A stable resonator for a ring-down cavity spectroscopy cell having an optic axis, the resonator comprising:

a first Brewster's angle retroreflector prism having greater than two total internal reflection surfaces; and a second Brewster's angle retroreflector prism having a plurality of total internal reflection surfaces and being disposed in alignment with the first prism along the optic axis of the resonator;

wherein radiation enters and leaves a surface of the one of the prisms nearly at Brewster's angle to the normal of the prism surface, and wherein the prisms are formed from at least one of fused silica, diamond, calcium fluoride, and yttrium aluminum garnet.

* * * * *